(12) United States Patent
Kraft (10) Patent No.: US 6,730,921 B2
(45) Date of Patent: May 4, 2004

(54) ION BEAM SYSTEM FOR IRRADIATING TUMOR TISSUES

(75) Inventor: Gerhard Kraft, Darmstadt (DE)

(73) Assignee: Gesellschaft fuer Schwerionenforschung mbH, Darmstadt (DE)

( * ) Notice: Subject to any disclaimer, the term of this patent is extended or adjusted under 35 U.S.C. 154(b) by 4 days.

(21) Appl. No.: 10/204,577

(22) PCT Filed: Mar. 7, 2001

(86) PCT No.: PCT/EP01/02575

§ 371 (c)(1),
(2), (4) Date: Dec. 4, 2002

(87) PCT Pub. No.: WO01/66187

PCT Pub. Date: Sep. 13, 2001

(65) Prior Publication Data

US 2003/0141460 A1 Jul. 31, 2003

(30) Foreign Application Priority Data

Mar. 7, 2000 (DE) .......................... 100 10 523

(51) Int. Cl.[7] .................................. A61N 5/10
(52) U.S. Cl. ..................................... 250/492.1
(58) Field of Search ................... 250/492.3, 309, 250/492.2, 505.1; 204/192.34; 378/65

(56) References Cited

U.S. PATENT DOCUMENTS

| | | | | |
|---|---|---|---|---|
| 4,870,287 A | * | 9/1989 | Cole et al. | 250/492.3 |
| 5,012,111 A | * | 4/1991 | Ueda | 250/492.3 |
| 5,260,581 A | * | 11/1993 | Lesyna et al. | 250/492.3 |
| 5,329,567 A | * | 7/1994 | Ikebe | 378/20 |
| 5,349,198 A | * | 9/1994 | Takanaka | 250/492.3 |
| 6,614,038 B1 | * | 9/2003 | Brand et al. | 250/492.3 |

FOREIGN PATENT DOCUMENTS

| | | |
|---|---|---|
| EP | 0 864 337 A | 9/1998 |
| EP | 0 911 064 A | 4/1999 |

OTHER PUBLICATIONS

Graffman S.; Jung B; Larsson B, "Design Studies for a 200 MeV Proton Clinic for Radiotherapy", *Proceedings of the 6th International Cyclotrons Conference*, Nr. 9, 1972, pp. 603–615, no month.

Chu W et al, "Instrumentation for Treatment of Cancer Using Proton and Light–Ion Beams", *Review of Scientific Instruments, American Institute of Physics, New York US*, Bd. 64, Nr. 8, Aug. 1, 1993, pp. 2055–2122.

Pedroni E, "Beam Delivery", *Hadrontherapy in Oncology: Proceedings of the International Symposium on Hadrontherapy*, XX,XX, 1994, pp. 434–452, no month.

* cited by examiner

Primary Examiner—John R. Lee
Assistant Examiner—Johnnie L Smith, II
(74) Attorney, Agent, or Firm—Frommer Lawrence & Haug LLP; Ronald R. Santucci (57) ABSTRACT

The invention relates to an ion beam system for irradiating tumor tissues at various irradiation angles in relation to a horizontally arranged patient couch and to a method of carrying out ion irradiations, wherein the patient couch has an apparatus for rotation about a vertical axis and the ion beam system has at least one of the following irradiation systems: a first irradiation system having an asymmetrical scanning system of fixed location, which has a central ion beam deflection region for deflection angles of up to ±15° with respect to the horizontal direction and makes possible scanning of a tumor volume in the central ion beam deflection region, and which has an additional lifting device for the patient couch; a second irradiation system, which has an ion beam deflection apparatus for a deflection angle greater than the first irradiation system and a symmetrical scanning unit for scanning the tumor volume, which scanning unit is arranged downstream of the ion beam deflection apparatus and is arranged to pivot synchronously with the deflection angle of the ion beam deflection apparatus.

20 Claims, 6 Drawing Sheets

ION BEAM SYSTEM FOR IRRADIATING TUMOR TISSUES

This application is a 371 of PCT/EP01/02575 filed on Mar. 7, 2001, now WO 01/66187 A1 published Sep. 13, 2001, and claims priority benefits of German application, DE 100 10 523.8 filed Mar. 7, 2000.

The invention relates to an ion beam system for irradiating tumour tissues and to a method of operating the system, in accordance with the preambles of the independent claims.

From U.S. Pat. No. 4,870,287 there is known a proton beam system for the selective production and transport of proton beams from a single proton source, via an accelerator, to a plurality of patient treatment stations, each of the treatment stations having a rotatable drum structure, hereinafter referred to as a gantry. In the known system, that gantry delivers the proton beam at various irradiation angles to a patient, who is arranged in a fixed position on a patient couch. A summary of gantry systems by Pedroni is known, from "Beam delivery" in Hadron Therapy in Oncology, Editors U. A. Maldi and B. Larson, Elsevier 1994, pages 434–452.

As long as such ion beam systems for irradiating tumour tissues operate with the lightest ion of the periodic system, namely the hydrogen ion or proton, the deflection magnets for a gantry and the masses of the latter are relatively small and manageable. However, when heavier ions such as the carbon ion, or others, are to be used, deflection magnets that are several times larger have to be used in order to direct the highly accelerated ions from the axis of a gantry to the periphery of the gantry and back to the gantry centre, where the patient is positioned. At the same time, correspondingly large masses have to be provided in the gantry as a counterweight to the deflection magnets, with the result that the rotating gantry structure, which has to be rotated and controlled with an accuracy of a few millimeters, weighs several hundred tonnes. As the ion mass number increases, so the gantry solution that has been favoured becomes heavier and less manageable and requires ever larger buildings for accommodating the treatment systems.

The aim of any beam therapy is to deposit as high a dose of radiation as possible in a narrowly circumscribed region—the tumour volume—and, as far as possible, to spare the surrounding healthy tissue. In customary X-ray therapy, because of the exponential decay of the photon dose with the depth of penetration in the conventional subcutaneous beam therapy of relatively deep-lying tumours, a high localised dose can be achieved only by directing the beam at the tumour volume from several directions in an intersecting irradiation technique. As a result, the involvement of healthy tissue in front of and behind the tumour volume is reduced. In clinical practice, two or three entry angles are usual and, with an inverse dose plan in the case of intensity-modulated therapy using photons, up to nine or ten entry channels, that is to say irradiation angle positions, are often planned. Such multi-field irradiations are feasible especially using the known gantry systems.

In a manner analogous to such photon beam therapy, a plurality of entry ports are also desirable in ion beam therapy although, as a result of the inverted dose profile of the ion beams, the dose in the entry channel is smaller than the dose in the region of the tumour volume. However, distribution of the unavoidable entry dose over a plurality of irradiation angles would, in the case of ion beam therapy too, signify a further clinical advantage. The known ion beam systems for proton beam treatment are therefore provided with irradiation application from all directions by means of appropriate gantry systems.

The gantry systems known from the Patent Specification U.S. Pat. No. 4,870,287 to that extent correspond to the gantry systems from photon and X-ray therapy. They first deflect the beam away from the patient axis and then bend it back at 90° to the patient. Variable irradiation angles are in that case achieved by means of the fact that the entire deflecting system is rotated through 360° along the beam direction with the aid of the gantry. The mechanical rotation serves the purpose, above all, of not having to vary the settings of the magnets and of having only to carry out mechanical rotation. However, that advantage of simple mechanical rotation without variation of the settings of the electromagnets holds only for as long as the gantry system uses a divergent ion beam for treatment. When a concentrated pencil-thin ion beam is produced, however, with an active scanning system being used for scanning the tumour volume, the magnetic field is no longer constant and unvarying, because the beam energy and, as a result, the magnetic constancy have to be utilised in accordance with the requisite energy steps having to be used for that pencil beam.

As a result, the main reason for a gantry having fixed magnet settings is no longer present, especially as, for the scanning system, the pencil beam already has to be deflected in an X and Y direction orthogonal to the central ion beam deflection region.

Furthermore, experience with the proton beam therapy system known from the Patent Specification U.S. Pat. No. 4 870 287 shows that, in the case of ion beam therapy of deep-lying tumours, not all the possible radiation-entry angles of a gantry are used with equal frequency. Rather, it has been found that there is a large range of seldom used irradiation angle zones because frequently occurring kinds of tumour necessitate frequently recurring restricted angle settings of the gantry. To that extent it has been found that conventional gantry systems do not constitute optimum solutions-for ion beam therapy because a large portion of the possible irradiation angles of a gantry remain little-used.

It is characteristic of the known and planned ion therapy systems that the particle beam is directed through the gantry system at a fixed angle and variation of the angle can be achieved only mechanically, by rotating the entire system. Because of the high energy of the particles—200 MeV for protons and approximately 400 MeV/U for carbon ions— and because of the large-area apertures necessary for scanning of the ion beams, deflection magnets having a high magnetic field strength and large-area apertures are necessary. That means that the electromagnets reach considerable dimensions and weight. A barrel-shaped gantry for carbon ions is accordingly designed for a radius of 7 m and a length of 15–20 m and a weight of 300–400 t, of which about 50 t alone is attributable to a concrete weight acting as a counterweight to the magnets. In the case of such considerable weights, the tolerances of the bearings and, as a result, the positional accuracy of the beam become increasingly important. In the case of the patient, however, the tolerance limits are in the millimeter range. In the case of the gantry systems constructed hitherto, such tolerance limits are difficult to meet.

In the construction of ion beam systems for hospitals, the construction of a plurality of gantry systems is a significant cost factor. The costs relate to the gantry itself, at more than 15 million DM per system, and to the construction of suitable operational rooms of more than 14 m in height and width and more than 20 m in length, which means an enclosed space of more than 4,000 m³. Such rooms have to be shielded by thick-walled concrete. In addition, the planned use of ion scanning methods still constitutes an as yet unsolved problem with regard to the necessary mechanical precision. For that reason, in the case of an ion scanning method, the requisite precision of 1 mm has to be checked, verified and corrected after each setting and for each new treatment.

The problem of the invention is to overcome the disadvantages of the prior art for an ion beam system and to provide irradiation systems that, after reducing costs and saving space, meet the requirements with, at the same time, increased precision.

The problem is solved by the features of the subject-matter of the independent claims. Preferred developments of the invention are shown by the features of the dependent claims.

The solution to the problem is based upon the fact that the patient is fixed in a lying posture on a patient couch and this horizontal position is not changed before or during irradiation. This horizontal position on a patient couch has the advantage that uncontrolled organ movements—of the kind that disadvantageously occur in the case of a sitting position or on rotation during treatment—are avoided. That means that the apparatus provided for rotation of the patient couch is used solely for adjusting the irradiation angle but is not actuated during active irradiation. Accordingly, an irradiation angle for the lying patient can advantageously be composed of all possible angles ($4\pi$), with 360° positioning ($2\pi$) of the horizontal patient couch on the irradiation plane being possible by virtue of the apparatus for rotation of the patient couch and, in addition, with positioning of the beam direction through 180° ($\pi$) orthogonally thereto; that is to say, by means of the irradiation systems according to the invention, irradiation can be carried out from vertically above, and around the patient laterally, to vertically below. As a result, it is advantageously possible, in the case of the solution according to the invention, to dispense with a gantry that rotates through 360°; nor, because of the problem being addressed, is such a gantry desirable, because a gantry that rotates through 360° restricts the space around the patient and as a result hinders access as well as the installation of diagnostic units such as, for example, a PET camera.

For that purpose, the solution according to the invention has, in addition to an apparatus for rotation of the patient couch about a vertical axis, at least one of the following irradiation systems: a first irradiation system having an asymmetrical scanning system of fixed location, which has a central ion beam deflection region for deflection angles of up to ±15° with respect to the horizontal direction and makes possible scanning of a tumour volume in the central ion beam deflection region, and which has an additional lifting apparatus for the patient couch, and a second irradiation system, which has an ion beam deflection apparatus for a deflection angle range greater than the first irradiation system and a symmetrical scanning unit for scanning the tumour volume, which scanning unit is arranged downstream of the ion beam deflection apparatus and is arranged to pivot synchronously with the deflection angle of the ion beam deflection apparatus.

Preferably, the ion beam system has at least two first irradiation systems and a second irradiation system, each in a separate irradiation room. That preferred division between two irradiation systems having restricted deflection angles of up to ±15° takes into account the fact that two thirds of tumour tissue treatments can be dealt with by using such an ion beam system and accordingly, in those irradiation systems having deflection angles restricted to ±15°, an asymmetrical scanning system, which in the X direction covers the width of the tumour volume and in the Y direction not only takes account of the depth of the tumour volume but also, as a result of enlargement of the defelction magnet system in the Y direction, extends the central ion beam deflection range to ±15° and at the same time, in the region of the central ion beam deflection region, makes possible scanning the depth of the tumour volume. For that purpose, the patient couch is provided with a lifting means in addition to the rotating means in order that it can be positioned at the deflection angle or irradiation angle of the central ion beam deflection region. The remaining portion of approximately one third of patients, for whom larger central ion beam deflection regions are required, are-treated using a second irradiation system, which can, independently of a scanning unit, initially with the aid of external deflection magnet units, deflect the ion beam up to ±90° with respect to the horizontal plane. A symmetrical scanning unit for scanning the tumour volume is pivoted synchronously with the deflection angle of the ion beam deflection apparatus of that second irradiation system, in the same direction as the deflection angle, so that the deflection magnet for such large deflection angles and the aperture of the magnet can be kept small and, likewise, the symmetrical scanning unit needs to be dimensioned only for deflecting and for scanning the tumour volume, which means a considerable saving in terms of weight and volume compared with the previously proposed gantry systems.

Because the preparation, and fixing in position, of the patient on the patient couch takes most of the time in the overall irradiation cycle in an ion beam system for irradiating tumour tissues, the ion beam system has at least one preparation room per irradiation system, each having a patient couch. Preferably, two or more preparation and aftercare rooms per irradiation system can be used. The number of requisite irradiation rooms accordingly increases with the number of irradiation systems used, and the number of preparation rooms increases with the time required for fixing a patient in position on the horizontal patient couch as a proportion of the actual irradiation procedure in the irradiation room.

Whereas, for an irradiation angle of between −15° and +15°, only one asymmetrical scanning unit of the first irradiation system is required and, except for setting the lifting and rotation of the patient couch, only the excitation current for one of the deflection magnets of the scanning system has to be made available and an extended exit window for the ion beam from the asymmetrical scanning system has to be provided, there is used, in a preferred, embodiment of the invention for the second irradiation system, an ion beam deflection apparatus of fixed location having a variable deflection angle, which apparatus is arranged to the side of the patient couch, the patient couch having an additional lifting apparatus, which overcomes substantially greater height differences than the lifting apparatus of the first irradiation system. The deflection magnet required for those larger irradiation angles can, however, be provided with a smaller aperture because the pencil-shaped ion beam passes the deflection magnet without undergoing prior deflection by a scanning unit in the X direction. Only after deflection is there then connected an appropriately dimensioned symmetrical scanning unit, which is arranged to pivot together with the deflection angle so that again the entire tumour volume can be scanned within the central ion beam deflection region.

Alternatively to the ion beam deflection magnet arranged to the side of the patient couch, that magnet can also, in a further embodiment of the invention, be arranged vertically above the patient, and the patient couch can be provided, not with a lifting apparatus, but with an apparatus that is displaceable laterally in the horizontal plane. That preferred alternative embodiment of the invention also makes it possible, without a rotating gantry, for a large range of radiation angles to be available for treating tumours.

In a further preferred embodiment of the invention, the second irradiation system has an ion beam deflection apparatus, having a variable deflection angle, which is displaceable on a horizontal linear track, and the patient couch is fixed in all directions laterally. That means that the patient couch has neither a lifting apparatus nor a means of displacement in the two axes of the horizontal plane. Only rotation about the vertical axis is possible, in order to fix the patient couch in position at an appropriate angle of rotation with respect to the irradiation direction. The horizontal linear track, on which the ion beam deflection apparatus slides displaceably, can be arranged above or below the patient, the excitation current in the magnet at the same time varying together with the displacement in order to deflect the ion beam at various angles towards the patient fixed in position.

In a further preferred embodiment of the invention, the second irradiation system has an ion beam deflection apparatus of fixed location having a variable deflection angle and has an ion beam deflection apparatus, having a variable deflection angle, which is displaceable on a vertical linear track. The two variable deflection angles are so matched to one another that the patient couch can remain in a fixed position laterally and, despite a varying treatment angle, no lateral displacement of the patient couch is necessary. The scanning unit is arranged downstream of that ion beam deflection apparatus which is displaceable on a vertical linear track and can consequently be of completely symmetrical construction in order to scan the tumour volume. This solution has the advantage over horizontal displaceability of the ion beam deflection apparatus that, for the vertical linear track of the displaceable ion beam deflection apparatus, only the deflection magnet has to be provided with a lifting apparatus. Accordingly, whilst the patient remains in his fixed position without lateral displacement, for positioning of the ion beam, a second deflection magnet is, in this case, moved up and down using a lifting apparatus in order to vary the irradiation angle. Once the irradiation angle has been set, it remains unchanged and constant during irradiation; nor is the patient further moved during irradiation.

In a further preferred embodiment of the invention, the second irradiation system has an ion beam deflection apparatus that is linearly displaceable at an angle $\alpha$ with respect to the horizontal direction on a sloping linear track, for a deflection angle range of from $-\alpha$ to $-(\alpha+90°)$, whilst the patient couch remains fixed in position laterally. For that purpose, the ion beam entering the treatment room horizontally is first deflected at an angle $\alpha$ towards the linearly displaceable ion beam deflection apparatus and that ion beam deflection apparatus, which requires only a linear displacement mechanism, directs the ion beam at the patient at a predetermined angle. That angle can range from 0 to 90° and can also, in a corresponding alternative arrangement, be arranged from 0 to −90°. In the first case, the sloping linear track is oriented from beside the patient to above the patient and, in the other case, the sloping linear track, on which the ion deflection apparatus slides, is displaced from a position to the side of the patient to a position below the patient. As a result of such a second irradiation system and a linearly displaceable ion beam deflection apparatus, it is possible to dispense with the resource-intensive construction of a gantry, and the following advantages are essentially achieved:

1. greater mechanical stability because of the linear movement on a sloping plane compared to rotation of a gantry;
2. omission of compensating weights that are otherwise necessary;
3. comparatively lighter weights for all moving parts;
4. comparatively lighter dipole magnets because only small apertures are necessary;
5. reduction of the enclosed, shielded irradiation room to approximately 600 $cm^3$, that is to say less than a quarter of the space for a rotating gantry; and
6. less restriction of the space around the patient couch and, consequently, improved possibilities for setting up other monitoring systems such as PET (photon emission topography device).

The same advantages can be achieved when, in a further preferred embodiment of the invention, the second irradiation system has an ion beam deflection apparatus of fixed location having a variable deflection angle and, in addition, an ion beam deflection apparatus which is linearly displaceable at an angle $\alpha$ with respect to the horizontal direction on a sloping linear track, for a deflection angle range of from $-\alpha$ to $-(\alpha+90°)$, whilst the patient couch remains fixed in position laterally. In that embodiment, provision is made for the ion beam to enter the treatment room above the patient and to be deflected at various deflection angles by an ion beam deflection apparatus of fixed location, and that in turn deflects the ion beam towards the patient by means of the second ion beam deflection apparatus, which is displaceable on a sloping linear track. In that embodiment too, the apertures are small, because a symmetrical scanning unit is arranged downstream of the displaceable ion beam deflection apparatus and in turn pivotally follows the deflection angle of the ion beam.

In a preferred embodiment of the invention, the angle $\alpha$ of the sloping linear track is 45°. That sloping track at 45° results in the fact that the patient can attain all irradiation angles in the quadrant of a circle from the side of the patient to vertical with respect to the patient, without the patient couch having to be moved.

For the purpose of deflecting the ion beam from the horizontal direction to a sloping track, the second irradiation system preferably has a first deflection magnet for the highly accelerated horizontal ion beam. A second deflection magnet, which belongs to the displaceable ion beam deflection apparatus, preferably directs the beam from the sloping linear track to a horizontal direction, and a suitable magnetic deflection system arranged downstream or a solenoid magnet causes further deflection between 0 and 90° with simultaneous movement of the entire ion beam deflection apparatus in dependence upon the setting of the excitation current of the suitable magnetic deflection system or of the solenoid magnet.

A preferred embodiment of the first irradiation system provides a first deflection magnet for scanning the tumour volume in an X direction of the plane orthogonal to the central ion beam deflection region and a deflection magnet for deflection in the direction of the central ion beam deflection region in a Y direction of the plane orthogonal to the central ion beam deflection region with additional superimposition for scanning the tumour volume in that direction.

That embodiment of the first irradiation system has the advantage that no additional deflection magnets are necessary and most patients with tumours can be treated in such an embodiment of the first irradiation system having a restricted deflection angle.

The spacing between the deflection magnet in the Y direction, in the case of the first irradiation system, and the patient couch is preferably between 5 and 7 m. On the other hand, a spacing between the displaceable linear track of the solenoid magnet of the second irradiation system and the patient couch is preferably from 3 to 6 m, the symmetrical scanning unit, which is displaceable therewith, being arranged in that range between 3 and 6 m.

Where a lifting apparatus for the patient couch is required in one of the embodiments of the invention, it is also possible for the entire floor of the irradiation room to be raised together with the patient couch so that the patient still advantageously has the impression of being in a fixed position in a conventional treatment room and operational staff can treat the patient in a normal working position at any time before and after irradiation.

For measuring the position of, and monitoring, the scanning ion beam, the ion beam system preferably has, in each irradiation chamber, ionisation chamber measurement apparatuses and multiwire chamber measurement apparatuses. Those measurement apparatuses advantageously indicate both the intensity of an ion beam and also the location of an ion beam.

The entire ion beam system is so designed that, in a preferred embodiment, the irradiation systems are arranged in irradiation rooms that are themselves located compactly next to one another and in the shape of segments of a circle. That has the advantage that short ion beam paths, having few deflection magnets, have to be connected to the accelerator as the ion beam source. In addition, that arrangement advantageously allows expansion of the system at any time, should that become necessary later on. That results in a kind of radial construction of the entire ion beam system with a plurality of irradiation rooms as the optimum solution.

In a further preferred embodiment of the invention, the ion beam system is provided with a visual checking means for the patient couch in the irradiation room in order to monitor defined angle-of-rotation changes between various settings for multi-field irradiation. That visual checking means advantageously allows the co-ordinates of the patient system to be compared with those of the radiation room, and checked, after transfer to the irradiation position. Rotation of the patient couch, which may be necessary in the case of multi-field irradiation from various irradiation angles, can be controlled from the outside by means of the visual checking means.

In a further preferred embodiment of the invention, the irradiation system has locking apparatuses for taking up and positioning a patient couch in the irradiation room. Such locking apparatuses are mechanically complex devices which ensure that the patient couch is adjustable with millimeter accuracy in relation to the irradiation direction and the irradiation angle. The locking device moreover ensures complete coupling between take-up and positioning devices for the patient couch so that the ion beam can exactly scan the tumour tissue in the irradiation room.

A method of carrying out ion irradiation in an ion beam system of the present invention comprises the following method steps:

a) immobilisation of the patient on a horizontal patient couch in a preparation room of the ion beam system;
b) determination of the optimum irradiation angle for the irradiation therapy;
c) selection of the suitable first or second irradiation system;
d) adjustment of the deflection angles and the locations of the deflection apparatuses for the central ion beam deflection region;
e) moving-in, locking and adjustment of the patient couch relative to the predetermined optimum irradiation angle in an irradiation room;
f) carrying out irradiation, where appropriate with interruptions for changes in the position of the patient couch and/or in the deflection angles of the deflection apparatus for multi-field irradiation;
g) transfer of the patient back to an aftercare room; and
h) removal of the patient immobilisation.

In that method, the patient couch advantageously serves as a movable irradiation unit, that part of the patient which is to be irradiated being immobilised with respect to a mechanical carrier system. For that purpose, in the preparation room, the stereotactic system is linked to the patient and the position of the patient in relation to that system is verified, for example by means of X-ray images. That method step a) takes from 30 to 60 minutes per patient and is accordingly the most time-consuming part of treatment and, at the same time, requires highly qualified staff. For that reason, a plurality of preparation rooms are preferably provided per irradiation room. The transfer to the irradiation room that follows should not take a great deal of time. There, the irradiation unit, together with the patient, is mechanically locked into a given irradiation system.

After transfer to the irradiation room, the co-ordinates of the irradiation unit are compared with those of the irradiation room and checked; only then can the patient be irradiated. Any rotation of the patient couch which may be required in the case of multi-field irradiation can be controlled from the outside with the aid of the visual checking means preferably incorporated. After irradiation, the patient, together with his irradiation unit, is taken to an aftercare room and can be discharged after removal of the immobilisation.

Further advantages, features and possibilities for use of the invention will be described below in further detail with respect to exemplary embodiments with reference to the accompanying drawings.

Figure 1:
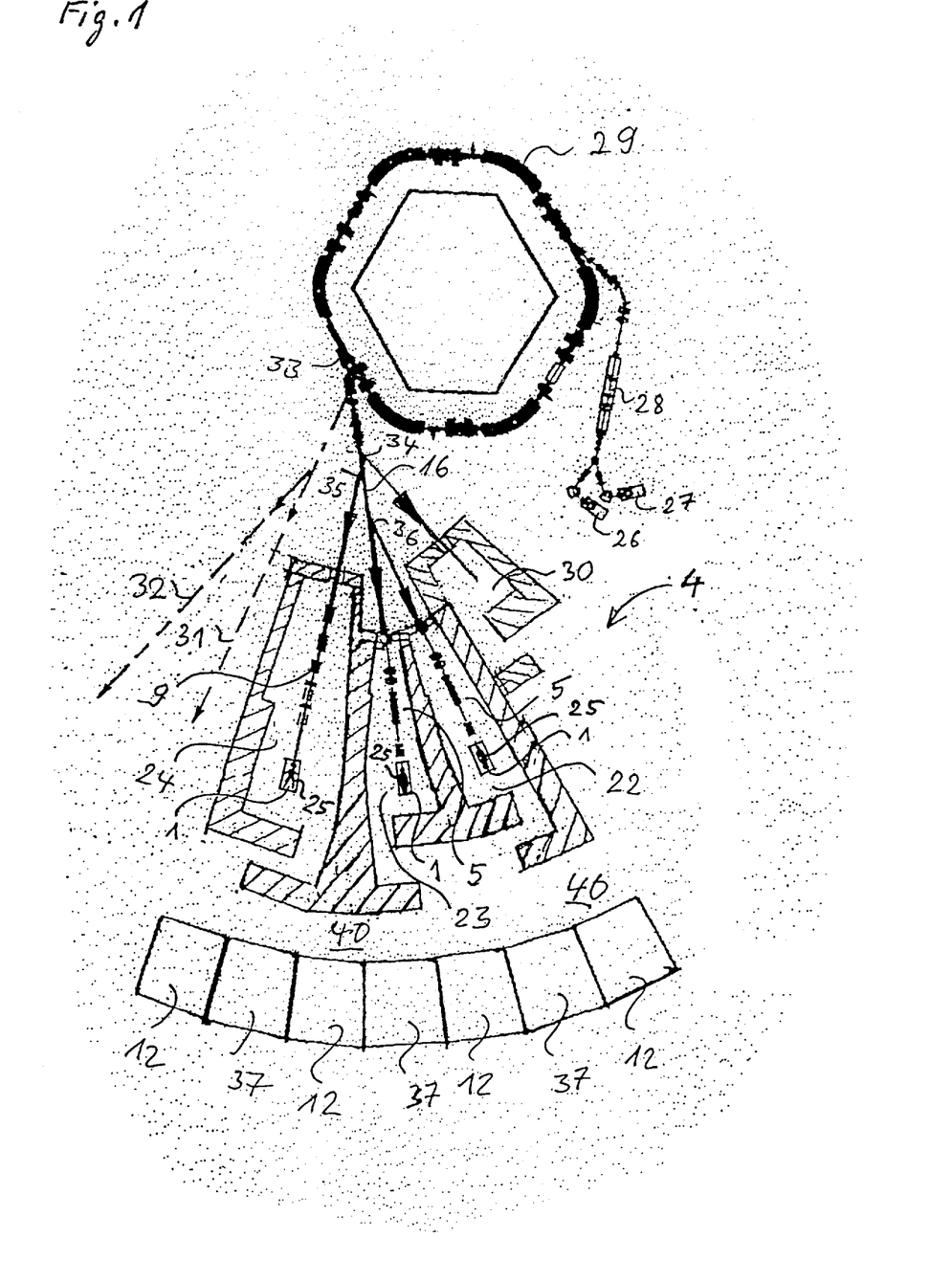
FIG. 1 is a representation, in diagrammatic form, of an ion beam system for irradiating tumour tissues in accordance with an embodiment of the present invention.

FIG. 1 is a representation, in diagrammatic form, of an ion beam system 4 for irradiating tumour tissues of a patient 25 on a patient couch 1 in accordance with an embodiment of the invention. Such an ion beam system has various ion sources 26, 27, which ionise various gases, select ions in a mass spectrometer and initially accelerate the selected ions in a linear acceleration chamber 28. The ions are then introduced into a synchrotron 29 for further high acceleration and, after assuming appropriate energy, they are coupled out from the synchrotron 29 in the form of an ion beam 16. The ion beam 16 can be deflected into irradiation rooms 22, 23, 24 and 30 arranged in the shape of segments of a circle. In the irradiation rooms 22, 23 and 24, for irradiating tumour tissues at various irradiation angles in relation to a horizontally arranged patient couch 1, tumour tissues are treated with ion beams. For that purpose, the ion sources 26 and 27 supply ions such as carbon ions, which, on passing through tissues, especially in the deceleration region of the ion track in the human body, can destroy tumour tissues especially effectively.

The ion beam system of this embodiment has a patient couch 1 having an apparatus for rotation about a vertical axis and has two irradiation rooms 22 and 23 having a first irradiation system, which has an asymmetrical scanning system of fixed location. That scanning system can deflect the horizontal ion beam into a central ion beam deflection region for deflection angles of up to ±15° with respect to the horizontal direction. At the same time, the asymmetrical scanning system can carry out scanning of the tumour volume in the central ion beam deflection region, for which purpose, by means of an additional lifting apparatus for the patient couch, the patient having the tumour tissue is raised into the region of action of the central ion beam deflection region.

Whereas the two irradiation rooms 22 and 23 are provided with an asymmetrical scanning system of that kind and a lifting apparatus for the patient couch 1, which can at the same time be rotated about its vertical axis, the third irradiation room 24 in this embodiment is provided with a second irradiation system, which has an ion beam deflection apparatus for a deflection angle range that is larger compared to the first irradiation system of the irradiation systems 22 and 23 and, arranged downstream of the ion beam deflection apparatus, a symmetrical scanning unit for scanning the tumour volume, which scanning unit can pivot synchronously with the deflection angle of the ion beam deflection apparatus.

The irradiation room 30 is a test and experimentation room, in which, especially, monitoring and measuring devices can be tested and adjusted. FIG. 1 also shows possibilities for expanding the ion beam system by the ion beam directions 31 and 32 (shown by the broken line) and preparation rooms 12, in which the patients can be prepared for the irradiation treatment. That ion beam system has been integrated from two irradiation systems to form one irradiation unit and is based on experiences with the known proton gantry system of U.S. Pat. No. 4,870,287, which is as yet the only system in the world in which clinical particle therapy is performed on high numbers of patients. Using the known system, about 1000 patients per year are irradiated, of whom two thirds to three quarters are irradiated solely in an irradiation angle range from either side of from 0 to 150 with respect to a horizontal patient couch 1. The rest of the rotational range of the known proton gantry system is not used for irradiation of that kind in a restricted angle range.

For that reason, in the present exemplary embodiment of an ion beam system according to FIG. 1, two of the three irradiation rooms are provided with a first irradiation system 5 according to the invention, which is optimised in terms of both price and weight and which avoids the gantry solutions, which have a high material and space requirement and are costly, and, by means of a new asymmetrical scanning system, allows a central ion beam deflection range of ±15° with respect to the horizontal direction.

For the remaining irradiations requiring a larger range of irradiation angles and fast, reproducible adjustment, a second irradiation system is provided, which likewise dispenses with a rotating gantry as known from the prior art, provided that it is possible for the linear gantry to be implemented technically. Otherwise, the irradiation room can, if necessary, be provided with a conventional rotary gantry. That device comprising a second irradiation system is provided in the irradiation room 24 of the example of an ion beam system according to FIG. 1. Both radiation systems, namely the asymmetrical scanning system and the second radiation system having a greater deflection angle range, have the advantage of compactness in the building dimensions required, as well as having high mechanical stability. As a result, the investment costs for construction are reduced and, in operation, additional checking measures and re-adjustments, as are necessary in the case of the gantry system, become superfluous.

Patient throughput is, in this case, dictated by the supply of patients and the checking of the position-of patients on the horizontal patient couch. In order to optimise the patient throughput without adversely affecting safety, the individual phases of work have to be separated from one another so that they can be carried out by the relevant specialists in a humane manner and without time pressure.

The method of carrying out irradiation in such a system according to FIG. 1 therefore comprises the following method steps:
a) immobilisation of the patient on a patient couch 1 in a preparation room 12 of the ion beam system 4;
b) determination of the optimum irradiation angle for the irradiation therapy;
c) selection of the suitable first or second irradiation system 5 or 9;
d) adjustment of the deflection angles and the locations of the deflection apparatuses for the central ion beam deflection region;
e) moving-in, locking and adjustment of the patient couch 1 relative to the predetermined optimum irradiation angle in the relevant irradiation room 22, 23, 24;
f) carrying out irradiation, where appropriate with interruptions for changes in the position of the patient couches 1 and/or in the deflection angles of the deflection apparatuses for multi-field irradiation;
g) transfer of the patient, on the patient couch 1, back to an aftercare room 37;
h) removal of the patient immobilisation on the patient couch 1.

The requirement for irradiation rooms 22, 23, 24 results from the indications of the patients. Starting from the basis of the distribution encompassed by the known proton treatment system of U.S. Pat. No. 4,870,287, which is equipped with three rotary gantries, results in the need for at least two irradiation rooms having asymmetrical scanning systems according to the first irradiation system 5 and a third irradiation room 24 having a second irradiation system having a larger irradiation angle than is possible with the first irradiation system. In order to avoid bottlenecks, the preparation rooms 12 of the ion beam system according to FIG. 1 are so arranged that each of the treatment rooms 22, 23, 24 can be reached from each preparation room 12. In accordance with experiences using the previous gantry systems, approximately 20 to 30% of tumour treatment cases require irradiation at an irradiation angle that is greater than 150. The ion beam system according to FIG. 1 should, accordingly, entirely satisfy the irradiation demands that have been made hitherto, without a single expensive rotating gantry system being required. Furthermore, it can be clearly seen in FIG. 1 that the irradiation rooms are located compactly next to one another, and extremely short beam paths having as few deflection angles as possible are connected to the acceleration devices 28 and 29 as the beam source.

The ion beam 16 from the accelerator is directed, by way of small-angle deflection means 33, 35 and 36 in the form of beam diverters, to three irradiation rooms 22, 23 and 24, which are located next to one another in the manner of sectors. Two adjacent irradiation rooms 22 and 23 are in each case provided with the first irradiation system 5, which is an asymmetrical scanning system. They are used for irradiation in the angle range from 0 to 15° with respect to the horizontal, that is to say for prostate patients and a large portion of brain tumour and basicranial tumour patients. The third irradiation room 24 is provided with an ion beam deflection apparatus for larger irradiation angles of between 0 and 90° with respect to the horizontal. The irradiation rooms 22, 23 and 34 are surrounded by a string of preparation and aftercare rooms 12 and 37, which are reached by way of a common corridor 40 between irradiation rooms 22, 23, 24 and preparation and aftercare rooms 12 and 37. That ion beam system according to the invention can be extended to the sides, if required, with further irradiation systems as indicated by the ion beam directions 31 and 32 (shown by the broken line).

Figure 2:
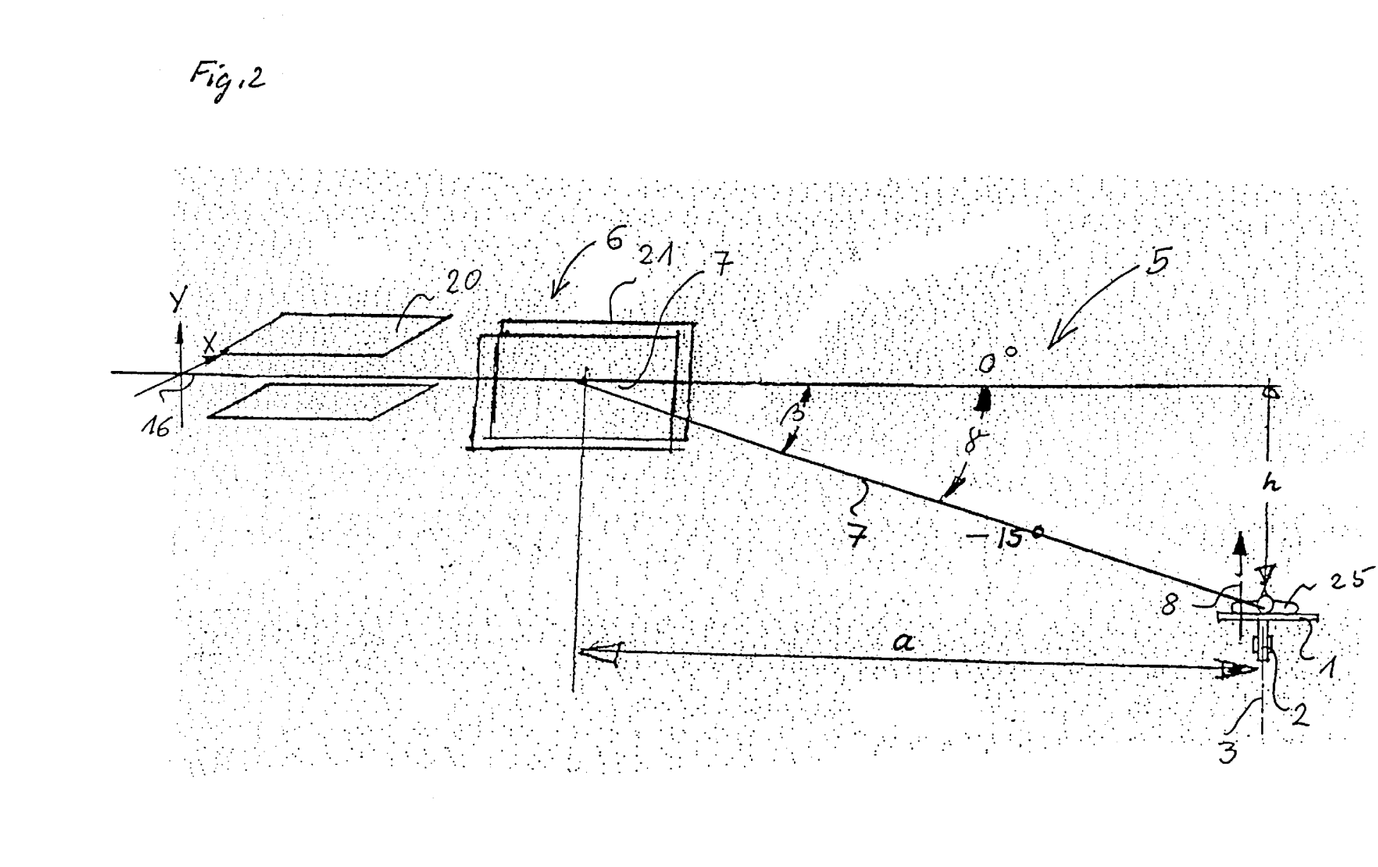
FIG. 2 is a representation, in diagrammatic form, of a first irradiation system having an asymmetrical scanning system of fixed location.

FIG. 2 is a representation, in diagrammatic form, of a first irradiation system 5 having an asymmetrical scanning system of fixed location consisting essentially of a deflection magnet 20 for horizontal scanning in the X direction of a plane located orthogonally to the central ion beam deflection region 7. Of the deflection magnet 20, only the active surfaces between two magnet shoes are represented (in diagrammatic form). The deflection in the X direction is relatively small compared to the shown deflection of −15° of the central ion beam deflection region 7, because the deflection of the asymmetrical scanning system in the X direction is intended solely for scanning the width of the tumour volume. On the other hand, the deflection magnet 21, which acts in the Y direction, is of substantially larger dimensions in order to provide a central ion beam deflection region of up to −15° in the Y direction with respect to the horizontal of 0°. Superimposed on that central ion beam deflection region 7 on irradiation of the tumour volume is a scan region (not shown) in the Y direction. Of that deflection magnet 21 too, only the active surfaces between two pole shoes are shown. That asymmetrical scanning system consequently produces relatively small irradiation angles γ of up to ±15°, the beam being guided at a sufficient height above the patient couch 1 and, as a result of activating a vertical deflection magnet 21, which is a constituent of the asymmetrical scanning system, being directed in a downwards direction in this exemplary embodiment of FIG. 2. Irradiation of the patient 25 is then performed on a patient couch 2 of variable height h, which is adjusted in accordance with the requisite irradiation angle γ.

A spacing of 5 m between the vertical scanning magnet 21 and the isocentre of the patient, where the tumour volume is located, gives rise to the height settings of Table 1.

TABLE 1

| "Gantry angle" | Patient height | Effective length |
|---|---|---|
| 0° | 0 cm | 5 m |
| +5° | −45 cm | 5.02 m |
| +10° | −90 cm | 5.08 m |
| +15° | −135 cm | 5.18 m |

Modifying the height of the patient couch by 1.35 m can be accomplished either by adjusting the patient couch alone or by adjusting the height of the floor in the entire irradiation room having the patient couch 1 or by means of lifting apparatuses both for the patient couch 1 and for the floor.

When there is a change in angle for the central ion beam deflection region by means of the vertical deflection magnet 21, a change in the effective length between the deflection magnet 21 and the isocentre also occurs; however, that change, being at most 20 cm, as can be seen from Table 1, remains relatively small and can be taken into account in the beam settings and irradiation plan. An overall range of 30°, namely from −15° to +15°, is possible in total for the vertical direction by means of the deflection magnet 21. For that purpose, it is merely necessary in this embodiment for the lifting apparatus 8 of the patient couch 1 to be provided with a sufficient lifting amplitude of up to 2.7 m. Except for the height adjustment of the patient couch by means of the lifting apparatus 8, there are no mechanically modifiable components of the beam guidance system in the case of this asymmetrical scanning system. In order to ensure that the beam has the necessary flexibility, the beam tube is constructed as a sector having the necessary width of approximately 20 cm and the necessary height of 1.35 m at a 15° deflection angle in the case of this example of FIG. 2 and is closed by a corresponding window of 20 cm×1.35 cm consisting of a textile support fabric having a sealing film located thereon. The detectors of the monitoring system, such as ionisation and multiwire chambers for the purpose of intensity and position measurement, can be distributed over the entire window area, which makes possible a checking measurement—free of mechanical influences—of the location and intensity of the ion beam in this first irradiation system.

Figure 3:
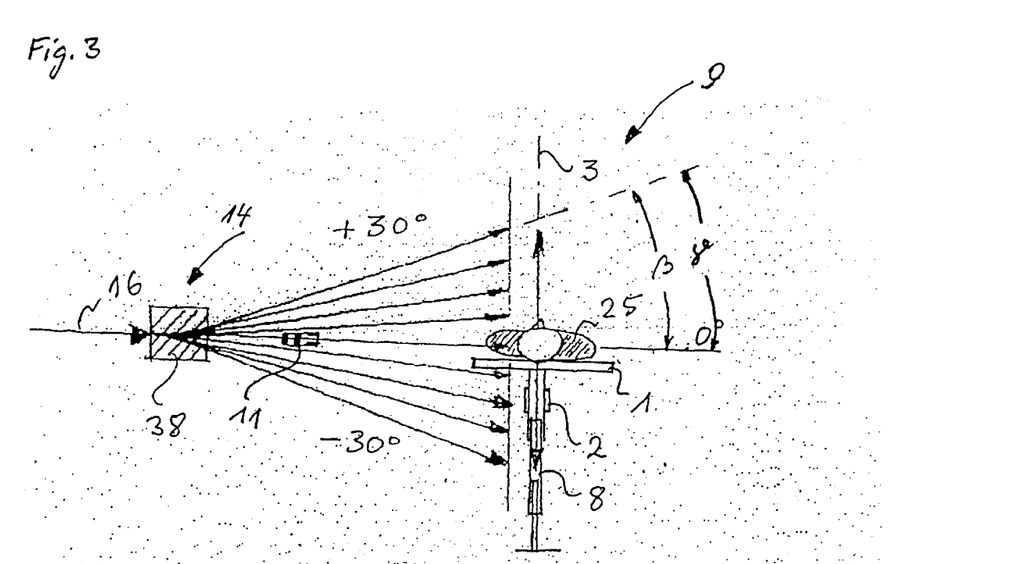
FIG. 3 is a representation, in diagrammatic form, of an embodiment of a second irradiation system having an ion beam deflection apparatus of fixed location and a vertical lifting apparatus for a patient couch.

FIG. 3 is a representation, in diagrammatic form, of an embodiment of a second irradiation system 9 having an ion beam deflection apparatus 14 of fixed location and a vertically displaceable patient couch 1. In the case of angles of more than 15°, which can be dealt with by the first irradiation system and which covers two thirds to three quarters of irradiation cases, irradiation angles of from −30° to +30° are in principle possible, without a resource-intensive rotating gantry, in accordance with FIG. 3, without the irradiation system itself being moved as is the case with the rotating gantry. Only the excitation current of the deflection magnet 38, which belongs to the ion beam deflection apparatus 14, is controlled. The scanning apparatus 11 itself can be of symmetrical construction, that is to say the deflection in both the X direction and the Y direction orthogonal to the central ion beam deflection region can be of the same order of magnitude in both directions. In the example of FIG. 3, the lifting apparatus 8 for the patient couch has been moved out just so far that the isocentre is at 0°. On changing the irradiation angle in the range from −30° to +30°, in this embodiment, not only is the patient moved by means of a height adjustment of the lifting apparatus 8 of the patient couch 1 but, together with the change in the irradiation angle γ, the symmetrical scanning apparatus 11 is pivoted.

Figure 4:
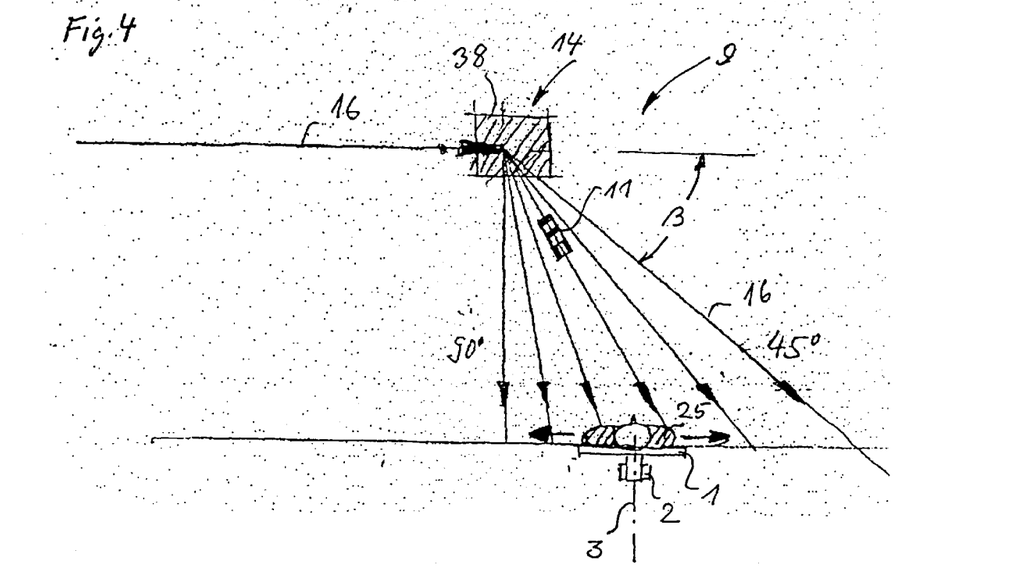
FIG. 4 is a representation, in diagrammatic form, of a further embodiment of a second irradiation system having an ion beam deflection apparatus of fixed location and a horizontally-displaceable-patient couch.

FIG. 4 is a representation, in diagrammatic form, of a further embodiment of a second irradiation system having an ion beam deflection apparatus 14 of fixed location and a horizontally displaceable patient couch 1. In contrast to FIG. 3, in this embodiment of the second irradiation system 9 the patient couch 1 is moved into the irradiation position horizontally, rather than vertically. The ion beam deflection apparatus 14 of fixed location is accordingly arranged above the patient and, by means of the deflection magnet 38, brings about deflection of the ion beam 16 from a horizontal source in order to provide the deflection angle β of from 45° to 90° to the horizontal. The symmetrical scanning apparatus 11 must also, at the same time, be pivoted synchronously with displacement of the patient couch 1 in order to be able to scan the tumour volume of the patient 25 completely.

Figure 5:
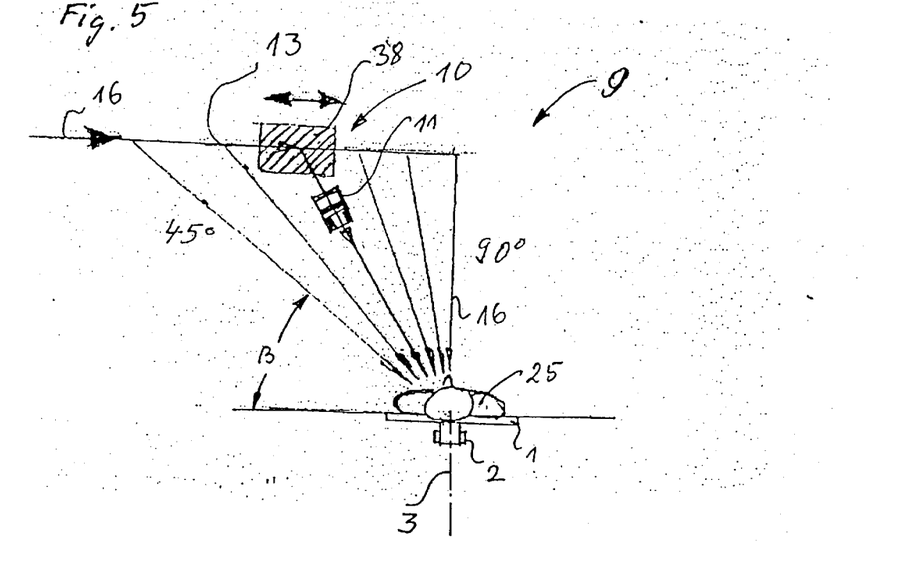
FIG. 5 is a representation, in diagrammatic form, of a further embodiment of a second irradiation system having a rotatable patient couch of fixed location and an ion beam deflection apparatus that is displaceable on a horizontal linear track.

FIG. 5 is a representation, in diagrammatic form, of a further embodiment of a second irradiation system 9 having a rotatable patient couch 1 of fixed location and an ion beam deflection apparatus 10 that is displaceable on a horizontal linear track 13. In this instance, where the horizontal linear track 13 for displacement of the ion beam deflection apparatus 10 is arranged above the patient, a deflection angle β of from 45° to 90° to the horizontal alignment can be achieved without having to move large masses, because the aperture of the deflection magnet 38 can be made extremely small, especially as the symmetrical scanning unit 11 is arranged downstream of that deflection magnet. In this embodiment too, besides the changing of the excitation current in the deflection magnet 38 and the movement of the latter on the horizontal linear track 13, the symmetrical scanning unit 11 has to be pivoted in accordance with the deflection angle β. The advantage of this embodiment is that the patient couch 1 can be of entirely fixed location and only be made rotatable about the vertical axis 3 in order to extend the range of the irradiation angle γ.

Figure 6:
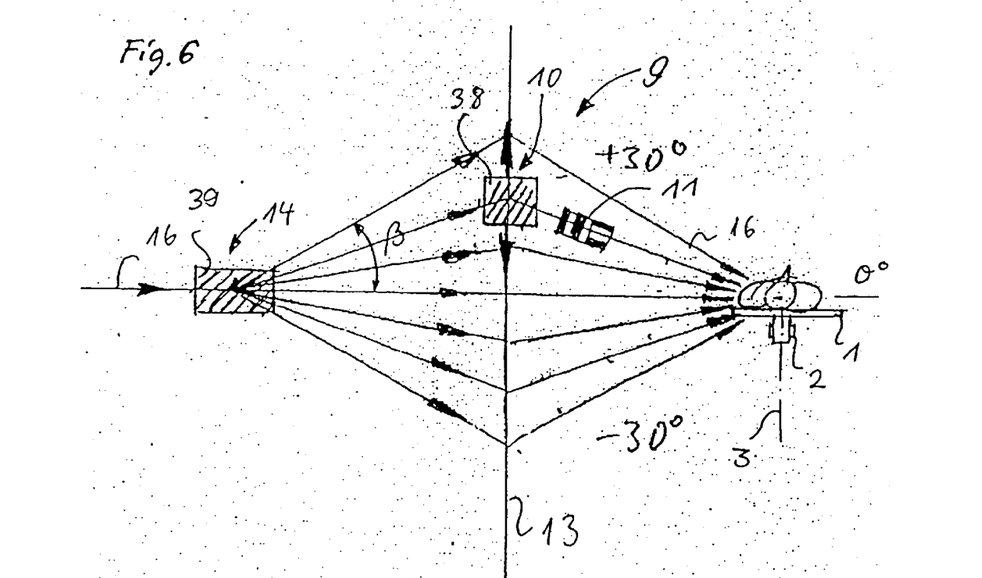
FIG. 6 is a representation, in diagrammatic form, of a further embodiment of a second irradiation system having a rotatable patient couch of fixed location and an ion beam deflection apparatus that is displaceable on a vertical linear track.

FIG. 6 is a representation, in diagrammatic form of a further embodiment of a second irradiation system 9 having a rotatable patient couch 1 of fixed location and an ion beam deflection apparatus 10 that is displaceable on a vertical linear track 13. Because the ion beam source supplies a horizontal ion beam 16, when an ion beam deflection apparatus that is displaceable on a vertical linear track is provided, a deflection magnet 39 of fixed location first deflects the ion beam from the horizontal at the deflection angle β and a deflection magnet 38 that is displaceable in a vertical linear direction can then direct the ion beam onto the patient couch 1 of fixed location. This embodiment according to FIG. 6 has the advantage that, again, only one lifting apparatus is required, namely for the vertically displaceable ion beam deflection apparatus 10, it being possible for such a lifting apparatus to be provided relatively cheaply and in space-saving manner by means of hydraulic mechanisms. The movement of the lifting apparatus must, in this instance too, be accompanied by that of a symmetrical scanning unit 11, which can be pivoted simultaneously with the deflection angle β.

Figure 7:
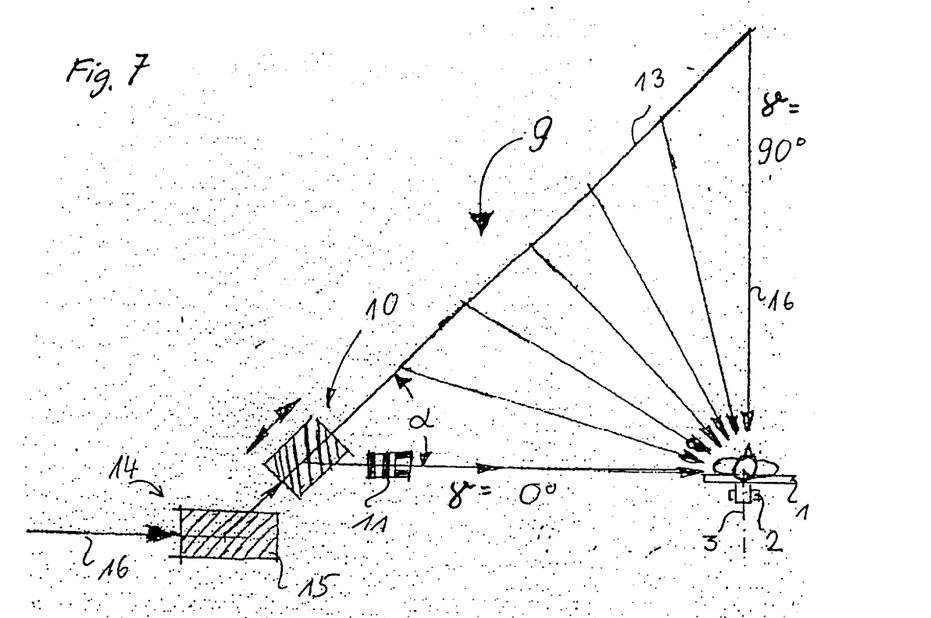
FIG. 7 is a representation, in diagrammatic form, of a further embodiment of a second irradiation system having a rotatable patient couch of fixed location and a displaceable ion beam deflection apparatus on a sloping linear track.

FIG. 7 is a representation, in diagrammatic form, of a further embodiment of a second irradiation system 9 having a rotatable patient couch 1 of fixed location and a displaceable ion beam deflection apparatus 10 on a sloping linear track 13. A sloping linear track 13 of that kind for an ion beam deflection apparatus 10 has the advantage that the angle restrictions, still discernible for the exemplary embodiments in FIG. 3 to FIG. 6, are now removed, in that, by means of this embodiment, irradiation angles γ can be accomplished starting from the horizontal 0° up to 90° without resource-intensive gantry systems being used. The embodiment according to FIG. 7 is based on the fact that the ion beam 16 enters the irradiation room in a horizontal direction below the position of the patient couch 1. A first deflection magnet 15 deflects the ion beam 16 into the direction of the sloping linear track 13 and the ion beam deflection apparatus 10, which can be moved on the sloping plane 13, so deflects it, as a result of variation of the excitation current of the electromagnet, at various angles, that in each case the rotatable patient couch 1 of fixed location at the isocentre is hit. In this instance too, the movement of the displaceable ion beam deflection apparatus 10 is accompanied by movement of a symmetrical scanning unit 11, which is in each case so pivoted that it remains oriented in the direction of the ion beam.

Figure 8:
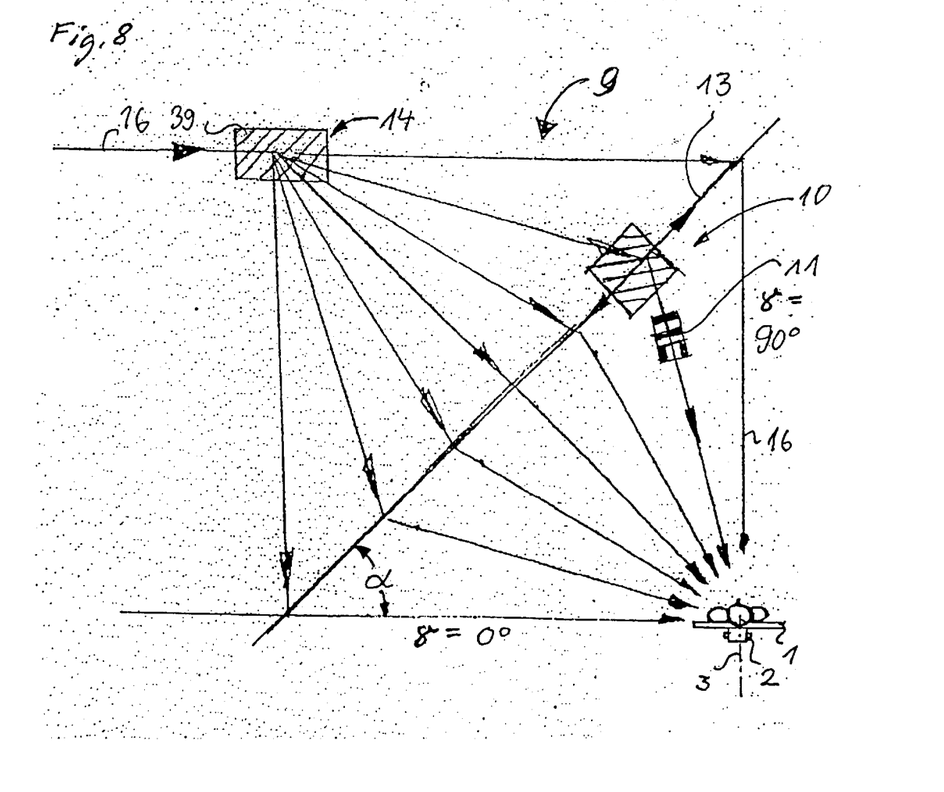
FIG. 8 is a representation, in diagrammatic form, of a further embodiment of a second irradiation system having a rotatable patient couch of fixed location and a combination of an ion beam deflection apparatus that is of fixed location and that is displaceable on a sloping linear track.

FIG. 8 is a representation, in diagrammatic form, of a further embodiment of a second irradiation system 9 having a rotatable patient couch 1 of fixed location and a combination of an ion beam deflection apparatus that is of fixed location and that is displaceable on a sloping linear track. For that purpose, in this embodiment it is assumed that the ion beam 16 is supplied to the irradiation room above the patient couch 1 and first meets a deflection magnet 39 of fixed location, which deflects the ion beam between 0° and 90° in relation to the horizontal direction. A displaceable ion beam deflection apparatus 10 can be moved on a sloping linear track 13 at an angle α and directs the ion beam 16 deflected by the deflection magnet 39 of fixed location, onto the patient couch 1. In this embodiment too, the movement of the displaceable ion beam deflection apparatus 10 is accompanied by movement of a symmetrical scanning unit 11, in order to scan the entire tumour volume in the isocentre on the patient couch 1.

Figure 9:
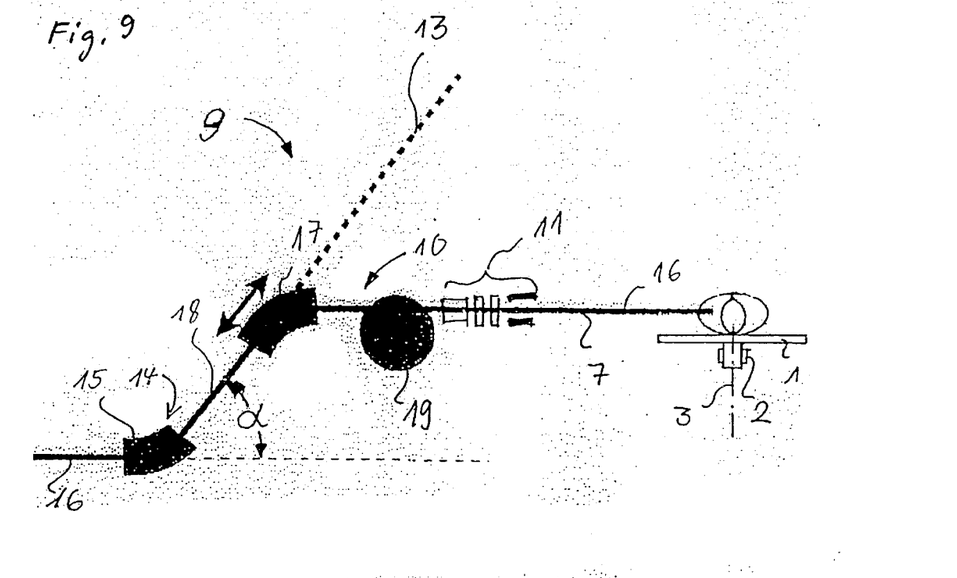
FIG. 9 is a representation, in diagrammatic form, of a further embodiment of a second irradiation system having a rotatable patient couch of fixed location and a sloping linear track inclined at an angle of 45° with respect to the horizontal direction for a displaceable ion beam deflection apparatus.

FIG. 9 is a representation, in diagrammatic form, of a further embodiment of a second irradiation system 9 having a rotatable patient couch 1 of fixed location and a sloping linear track 13 inclined at an angle of 45° with respect to the horizontal direction for a displaceable ion beam deflection apparatus 10. The ion beam deflection apparatus 10 in this instance consists of a deflection magnet of fixed location, which deflects the ion beam 16, which arrives in the irradiation chamber in the horizontal direction, into a sloping linear track, which is inclined at an angle α=45° with respect to the horizontal direction. The deflected ion beam 18 is then deflected, constant and unchanged, by a second deflection magnet 17, first into a horizontal direction. A solenoid magnet 19 arranged downstream can then, in dependence upon its excitation current, deflect the ion beam from 0° to 90°. In that respect, FIG. 9 shows the situation where the solenoid magnet 19 is not active and consequently the ion beam is guided horizontally towards the patient couch 1. Downstream of the solenoid magnet 19 there is arranged a symmetrical scanning unit 11, horizontally arranged in the position of FIG. 9, which can scan the tumour volume as a result of an appropriate deflection field in the X and Y direction orthogonal to the central ion beam deflection region 7.

Figure 10:
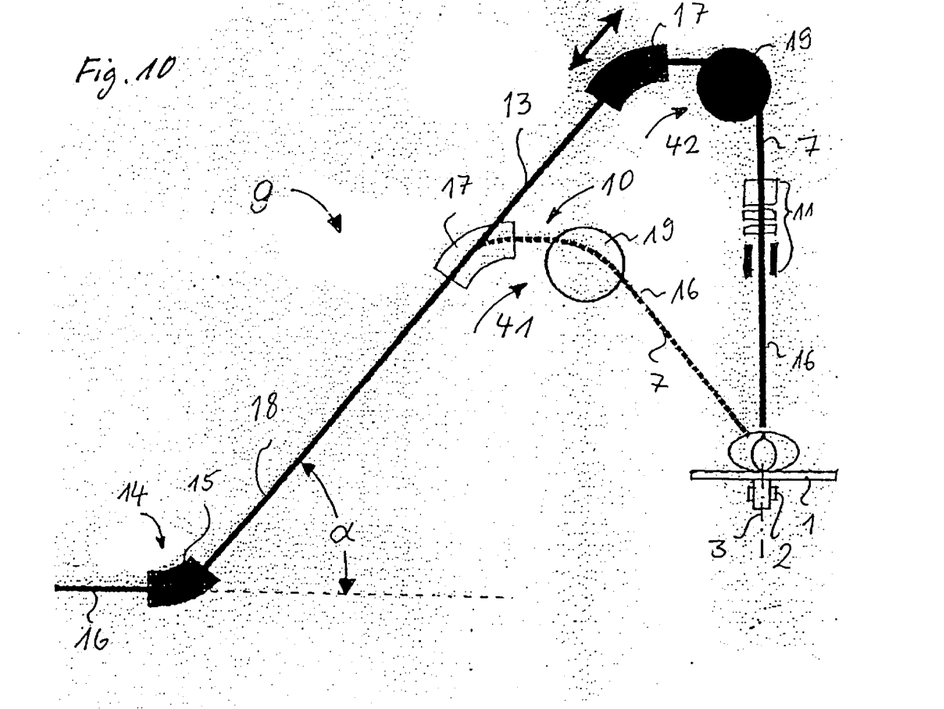
FIG. 10 is a representation, in diagrammatic form, of the embodiment shown in FIG. 9, in two further positions of the displaceable ion beam deflection apparatus.

FIG. 10 is a representation, in diagrammatic form, of the embodiment shown in FIG. 9, in two further positions 41 and 42 of the displaceable ion beam deflection apparatus 10. The middle position 41 (shown by a broken line) indicated by an ion beam 16 shows the same deflection action of the second deflection magnet 17 and the increased deflection action of the solenoid magnet 19, which in the second position 42 exhibits its maximum action by means of an ion beam 16 bent through 90°. In each case, the symmetrical scanning unit 11 is pivoted along with the ion beam 16 so that in all positions of the irradiation angle γ it is possible to scan the tumour volume completely.

As a result, by means of this 45° linear gantry, a resource-intensive rotation gantry system is avoided, with linear displacement of the magnet system on a sloping plane, as in this example on a 45° incline, being sufficient. In that arrangement, the beam is directed first from the horizontal plane to the 45° plane. On that plane, there has to be installed a set of movable magnets having a maximum deflection capacity of 135°. For irradiation from 0° (horizontally) the movable system is located at its lowermost point and, as a result of activation of a 45° dipole magnet, directs the beam at 0° at the patient.

In the case of vertical irradiation (90°), the movable magnet set must be moved to the upper end of the 45° sloping plane, and the second magnet deflection system, represented in this example by a solenoid magnet, is, in addition, activated to 90°. All angles between 0° and 90° can accordingly be accomplished by intermediate positions and appropriate magnet excitations. Irradiations between 90° and 180° are made possible by simply rotating the patient couch.

With a maximum height of 6 m above the patient couch 1, the ion beam scanning unit 1 can be accommodated downstream of the final dipole magnet. As a result, the apertures of the dipole magnets can be kept small and, as a result, the weight can be reduced substantially compared to the gantry solutions. The fundamental advantages of the system shown in FIGS. 9 and 10, having a sloping plane, have already been described in detail.

What is claimed is:

1. Ion beam system for irradiating tumour tissues at various irradiation angles (γ) in relation to a horizontally arranged patient couch (1),
wherein
the patient couch (1) has an apparatus (2) for rotation about a vertical axis (3); and the ion beam system (4) has at least one of the following irradiation systems:
a first irradiation system (5) having a symmetrical or asymmetrical scanning system (6) of fixed location, which has a central ion beam deflection region (7) for deflection angles (β) of up to ±15° with respect to the horizontal direction and makes possible scanning of a tumour volume in the central ion beam deflection region (7), and which has an additional lifting apparatus (8) for the patient couch (1), the lifting apparatus (8) and the apparatus (2) for rotation of the patient couch being adjustable for adaptation to the deflection angle (β) and being non-modifiable during irradiation;
a second irradiation system (9), which has an ion beam deflection apparatus (10), linearly displaceable and arranged to be fixed in terms of location, for a deflection angle (β) range greater than the first irradiation system (5) and a symmetrical scanning unit (11) for scanning the tumour volume, which scanning unit (11) is arranged downstream of the ion beam deflection apparatus (10) and is arranged to pivot synchronously with the deflection angle (β) of the ion beam deflection apparatus (10), an apparatus (2) for rotation of the patient couch (1) and a lifting apparatus (8) for the patient couch (1) being adjustable for adaptation of the patient couch (1) to the deflection angle (β) and being non-modifiable during irradiation.

2. Ion beam system according to claim 1,
wherein
the ion beam system (4) has at least two first irradiation systems (5) and a second irradiation system (9).

3. Ion beam system according to claim 1,
wherein
the ion beam system has at least one preparation room (12) per irradiation system (5, 9), each having a patient couch (1).

4. Ion beam system according to claim 1,
wherein
the second irradiation system (9) has an ion beam deflection apparatus (14) of fixed location and of variable deflection angle (β) arranged to the side of the patient couch (1); and the patient couch (1) has an additional vertical lifting apparatus (8).

5. Ion beam system according to claim 1,
wherein
the second irradiation system (9) has an ion beam deflection apparatus (14) of fixed location and of variable deflection angle (β) arranged vertically above the patient couch (1); and the patient couch (1) is displaceable in a horizontal direction.

6. Ion beam system according to claim 1,
wherein
the second irradiation system (9) has an ion beam deflection apparatus (10) of variable deflection angle (β) that is displaceable on a horizontal linear track (13); and the patient couch (1) is fixed in position laterally.

7. Ion beam system according to claim 1,
wherein
the second irradiation system (9) has an ion beam deflection apparatus (14) of fixed location and of variable deflection angle (β) and an ion beam deflection apparatus (10) of variable deflection angle (β) that is displaceable on a vertical linear track (13); and the patient couch (1) is fixed in position laterally.

8. Ion beam system according to claim 1,
wherein
the second irradiation system (9) has an ion beam deflection apparatus (10), linearly displaceable on a sloping linear track (13) at an angle α with respect to the horizontal direction, for a deflection angle (β) in the range from $-\alpha$ to $-(\alpha+90°)$; and the patient couch (1) is fixed in position laterally.

9. Ion beam system according to claim 1,
wherein
the second irradiation system (9) has an ion beam deflection apparatus (14) of fixed location and of variable deflection angle (β) and has an ion beam deflection apparatus (10), linearly displaceable on a sloping linear track (13) at an angle α with respect to the horizontal direction, for a deflection angle (β) in the range from $-\alpha$ to $-(\alpha+90\,°)$; and the patient couch (1) is fixed in position laterally.

10. Ion beam system according to claim 8,
wherein
the angle α of the sloping linear track is 45°.

11. Ion beam system according to claim 9,
wherein
the second irradiation system (9) has a first deflection magnet (15) for deflecting a highly accelerated horizontal ion beam (16), which deflects the ion beam (16), through the deflection angle α, to the sloping linear track (13), and has a second deflection magnet (17), which directs the deflected ion beam (18) from the sloping linear track (13), on which the second deflection magnet (17) is displaceable, back into the horizontal direction, and has a solenoid magnet (19), which is displaceable together with the second deflection magnet (17), for deflecting the ion beam (16) towards the patient couch (1) at a predetermined irradiation angle (8).

12. Ion beam system according to claim 1,
wherein
the first irradiation system (5) has a first deflection magnet (20) for scanning the tumour volume in an X direction of the plane orthogonal to the central ion beam deflection region (7) and has a deflection magnet (21) for deflecting in the direction of the central ion beam deflection region (7) in a Y direction of the plane orthogonal to the central ion beam deflection region (7) with additional superimposition for scanning the tumour volume in that direction.

13. Ion beam system according to claim 1,
wherein
the spacing between the deflection magnet (21) in the Y direction and the patient couch (1) of the first irradiation system (5) is between 5 and 7 meters.

14. Ion beam system according to claim 1,
wherein
the spacing between the displaceable linear track (13) of the solenoid magnet (19) and the patient couch (1) is from 3 to 6 meters and the co-displaceable magnetic scanning unit (11) is arranged in that region.

15. Ion beam system according to claim 1,
wherein
the entire floor of the irradiation room (22, 23, 24) is also raised when the patient couch (1) is raised.

16. Ion beam system according to claim 1,
wherein
the ion beam system (4) has ionisation chamber measurement apparatuses and multiwire chamber measurement apparatuses for measuring the location of, and monitoring, the scanning ion beam (16).

17. Ion beam system according to claim 1,
wherein
the irradiation systems (5, 9) are arranged in irradiation rooms (22, 23, 24) that are located next to one another compactly and in the shape of segments of a circle.

18. Ion beam system according to claim 1,
wherein
the ion beam system (4) has a visual checking means for the patient couch (1) in the irradiation room (22, 23, 24) in order to monitor defined angle-of-rotation changes between various settings for multi-field irradiation of the patient couch (1).

19. Ion beam system according to claim 1,
wherein
the irradiation systems (5, 9) have locking apparatuses for taking up and positioning a patient couch (1) in the irradiation room (22, 23, 24).

20. Method of carrying out ion irradiations in the ion beam system of claim 1, comprising the following method steps:
a) immobilization of a patient on a patient couch (1) in a preparation room (12) of the ion beam system (4),
b) determination of the optical irradiation angle for the irradiation therapy;
c) selection of the suitable first or second irradiation systems (5, 9),
d) adjustment of the deflection angles and the locations of the ion beam deflection apparatuses (10, 14) for the central ion beam deflection region (7),
e) moving-in, locking and adjustment of the patient couch (1) relative to the predetermined optimum irradiation angle in the irradiation room (22, 23, 24),
f) carrying out irradiation, where appropriate with interruptions for changes in the position of the patient couch (1) and/or in the deflection angles of the ion beam deflection apparatuses (10, 14) for multi-field irradiation;
g) transfer of the patient back to an aftercare room (37), and
h) removal of the patient immobilization on the patient couch (1).

* * * * *